(12) United States Patent
Lastovich et al.

(10) Patent No.: US 6,440,096 B1
(45) Date of Patent: Aug. 27, 2002

(54) MICRODEVICE AND METHOD OF MANUFACTURING A MICRODEVICE

(75) Inventors: Alexander G. Lastovich, Raleigh, NC (US); John D. Evans, Marina del Rey, CA (US); Ronald J. Pettis, Durham, NC (US)

(73) Assignee: Becton, Dickinson and Co., Franklin Lakes, NJ (US)

( * ) Notice: Subject to any disclaimer, the term of this patent is extended or adjusted under 35 U.S.C. 154(b) by 146 days.

(21) Appl. No.: 09/616,771

(22) Filed: Jul. 14, 2000

(51) Int. Cl.[7] .................................................. A61N 1/30
(52) U.S. Cl. ........................................ 604/27; 424/448
(58) Field of Search ...................... 604/21, 27, 132, 604/191, 68, 22; 424/448, 449; 264/313

(56) References Cited

U.S. PATENT DOCUMENTS

| | | |
|---|---|---|
| 5,250,023 A | 10/1993 | Lee et al. |
| 5,466,465 A * | 11/1995 | Royds et al. ................ 424/449 |
| 5,879,326 A | 3/1999 | Godshall et al. |
| 5,983,136 A * | 11/1999 | Kamen .......................... 604/21 |
| 5,993,412 A * | 11/1999 | Deily et al. .................... 604/68 |
| 6,126,637 A * | 10/2000 | Kriesel et al. ................ 604/132 |
| 6,183,434 B1 * | 2/2001 | Eppstein ........................ 604/22 |
| 6,322,808 B1 * | 11/2001 | Trautman et al. ............ 424/448 |
| 6,331,266 B1 * | 12/2001 | Powell et al. ................. 264/313 |
| 6,334,856 B1 * | 1/2002 | Allen et al. ................... 603/191 |

FOREIGN PATENT DOCUMENTS

WO    WO 97/48440    12/1997

* cited by examiner

*Primary Examiner*—Teresa Walberg
*Assistant Examiner*—Leonid M Fastovsky
(74) *Attorney, Agent, or Firm*—Eric M. Lee

(57) ABSTRACT

A device for monitoring, sampling or delivering a substance though the skin of a patient includes a support and a microdevice having at least one skin penetrating member. The support has a substantially flat bottom surface with the skin penetrating member extending beyond the bottom surface. An outlet port extends through the support to the bottom surface at a location between the skin penetrating member and the outer edge of the support for drawing a vacuum to enhance penetration of the skin. The device is produced by positioning the microdevice in a recess formed in the support and applying a bonding agent to wick into a gap formed between the microdevice and the wall of the recess.

46 Claims, 8 Drawing Sheets

MICRODEVICE AND METHOD OF MANUFACTURING A MICRODEVICE

FIELD OF THE INVENTION

The present invention relates to a microdevice and to a method of manufacturing the microdevice. The invention is further directed to a method and device for withdrawing or delivering a substance transdermally to a patient. The invention is also directed to a method and apparatus for enhancing the penetration of a microneedle array.

BACKGROUND OF THE INVENTION

Various devices have been proposed for sampling and delivering of substances such as pharmaceutical agents and drugs transdermally. Although the subcutaneous sampling and delivery methods using a cannula are effective for many applications, the pain normally induced by the cannula has prompted the development of less painful delivery methods.

The skin is made up of several layers with the upper composite layer being the epithelial layer. The outermost layer of the skin is the stratum corneum that has well known barrier properties to prevent molecules and various substances from entering the body and analytes from exiting the body. The stratum corneum is a complex structure of compacted keratinized cell remnants having a thickness of about 10–30 microns. The stratum corneum forms a waterproof membrane to protect the body from invasion by various substances and the outward migration of various compounds.

The natural impermeability of the stratum corneum prevents the administration of most pharmaceutical agents and other substances through the skin. Numerous methods and devices have been proposed to enhance the permeability of the skin and to increase the diffusion of various drugs through the skin to can be utilized by the body. Typically, the delivery of drugs through the skin is enhanced by either increasing the permeability of the skin or increasing the force or energy used to direct the drug through the skin.

Another method of sampling and delivering various substances through the skin is by forming micropores or cuts through the stratum corneum. By piercing the stratum corneum and delivering a drug to the skin in or below the stratum corneum, many drugs can be effectively administered. In a similar manner, some substances can be extracted from the body through cuts or pores formed in the stratum corneum. The devices for piercing the stratum corneum generally include a plurality of micron size needles or blades having a length to pierce the stratum corneum without passing completely through the epidermis. Examples of these devices are disclosed in U.S. Pat. No. 5,879,326 to Godshall et al.; U.S. Pat. No. 5,250,023 to Lee et al., and WO 97/48440.

The above-noted devices that include micron-sized needles or blades can be effective in delivering or sampling of substances in the body. However, these needles and blades having a length a few microns to a few hundred microns typically do not penetrate skin to a uniform depth. The natural elasticity and resilience of the skin will often result in the skin being deformed by the needles rather than pierced. A microneedle array when pressed against the skin often results in the outermost needles penetrating the skin while the innermost needles do not penetrate or only penetrate to depth less than the outermost needles.

The prior methods and devices for the transdermal sampling and administration of substances have exhibited limited success. Accordingly, a continuing need exists in the industry for an improved device for the sampling and administration of various drugs and other substances to the body.

SUMMARY OF THE INVENTION

The present invention is directed to a method and apparatus for the transdermal sampling or delivery of a substance though the skin of a patient. The invention is further directed to a method of manufacturing and assembling a device for delivering or withdrawing a substance through the skin of a patient. In particular, the invention is directed to a method and apparatus for delivering a pharmaceutical agent such as a drug or vaccine, to the stratum corneum of the skin to a sufficient depth where the pharmaceutical agent can be absorbed and utilized by the body.

Accordingly, a primary object of the invention is to provide a device having a skin penetrating member and to a method of penetrating the skin for sampling or delivering a substance through the skin substantially without pain to the patient.

Another object of the invention is to provide a device having a plurality of microtubes, needles, microneedles, blades or lancets for piercing the stratum corneum of the skin for withdrawing or delivering a substance though the skin of a patient.

A further object of the invention is to provide a device having at least one skin penetrating member and a device for enhancing the penetration of the skin.

Another object of the invention is to provide a device for sampling or delivering a substance to a patient where the device has a support and a microneedle device bonded to the support.

A further object of the invention is to provide a device for withdrawing or delivering a substance where the device includes a skin penetrating device and a vacuum port for applying a vacuum to enhance penetration of the skin by the skin penetrating device.

A still further object of the invention is to provide a method for enhancing skin penetration by a skin penetrating device in a target area by applying a vacuum to the surface of the target area and the skin penetrating device.

Another object of the invention is to provide a method of assembling a device comprising fitting a microdevice into a recessed area in a support and applying a bonding agent to the recess to wick between the microdevice and the support.

Still another object of the invention is to provide a method of bonding a microdevice to a support, where the support includes a recessed area and a channel having one end communicating with the channel, the method comprising fitting the microdevice in the recessed area and applying a bonding agent to the channel to flow into a gap between the support and the microdevice.

These and other objects of the invention are substantially attained by providing a method for forming a device for delivering or withdrawing a substance through the skin of a patient. The method comprises the steps of: providing a support having a bottom face with a recessed area having a dimension less than a dimension of said bottom face, positioning a skin penetrating device in said recessed area of said support. The skin penetrating device has a base and at least one skin penetrating member, the base has a dimension less than said dimension of said recessed area. A bonding agent is applied to at least one location between said support and said base in said recessed area, where the bonding agent has a viscosity to wick between the base and the support.

The objects and advantages of the invention are further attained by providing a method of withdrawing a substance or delivering a substance through the skin of a patient, said method comprising providing a support having a central passage, a bottom face, and a skin penetrating device on said bottom face, said central passage being in communication with said skin penetrating device, positioning said support on the skin of a patient with said bottom face of said support and said skin penetrating device contacting said skin, reducing the pressure in an area between said support and said skin to draw said skin toward said skin penetrating device and to cause said skin penetrating device to penetrate said skin, and withdrawing or delivering a substance through the skin of said patient.

Another object of the invention is to provide a device for delivering or withdrawing a substance from a patient, said device comprising: a support member having a bottom face and a recessed area having a dimension less than a dimension of said bottom face, a skin penetrating device having a base and at least one skin penetrating member, said base being positioned within said recessed area of said support, and a bonding material attaching said skin penetrating device to said support member and filling a space between said recessed area and said base of said skin penetrating device.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings in which.

DETAILED DESCRIPTION OF THE PREFERRED EMBODIMENTS

Figure 1:
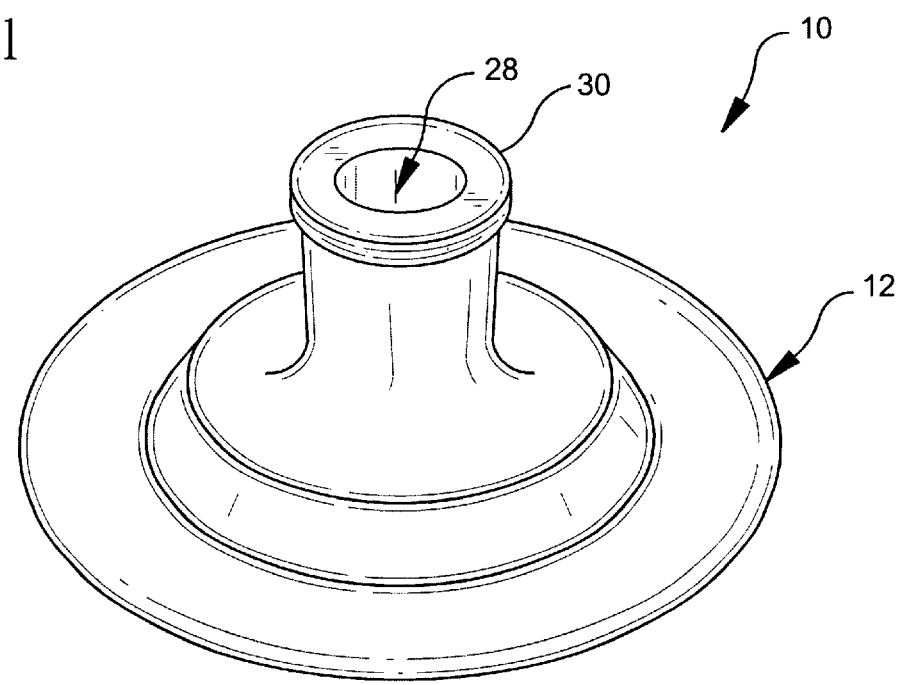
FIG. 1 is a perspective view of the sampling or delivery device in accordance with a first embodiment of the invention.

The present invention is directed to an intradermal device for sampling, monitoring or delivering a substance through the skin of a patient. More particularly, the invention is directed to a sampling, monitoring or delivery device and to a method for sampling or administering a substance into or below the stratum corneum of the skin of a patient. The invention is further directed to a method of manufacturing the sampling, monitoring or delivery device.

As used herein, the term penetrate refers to entering a layer of the skin without passing completely through. Piercing refers to passing completely through a layer of the skin.

The device and method in one embodiment of the present invention are suitable for use in administering various substances, including pharmaceutical agents, to a patient, and particularly to a human patient. As used herein, a pharmaceutical agent includes a substance having biological activity that can be delivered through the body membranes and surfaces, and particularly the skin. Examples include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally to a patient include proteins, peptides and fragments thereof. The proteins and peptides can be naturally occurring, synthesized or recombinantly produced.

The device and method are also suitable for withdrawing a substance or monitoring the level of a substance in the body. Examples of substances that can be monitored or withdrawn include blood, interstitial fluid or plasma that can then be analyzed for analytes, glucose, drugs and the like.

Referring to the drawings, the invention is directed to a device 10, having a support 12 and a microdevice 14. The device 10 can be a monitoring device for monitoring a substance level in the body, a sampling device for withdrawing a sample from the body, or a delivery device for delivering a substance to the body.

Figure 2:
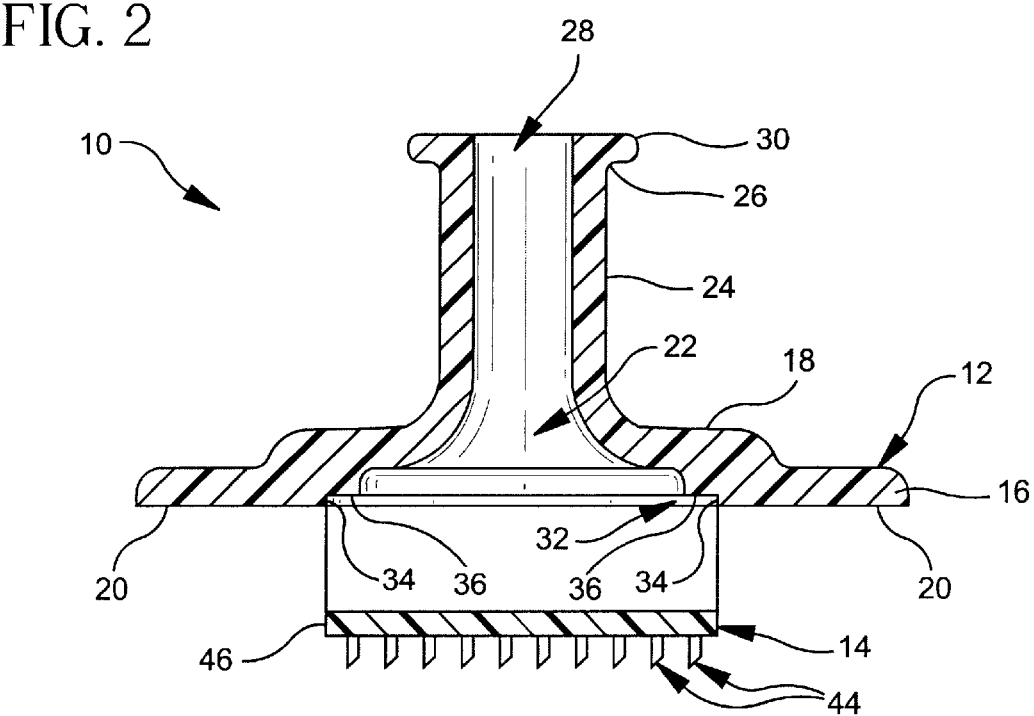
FIG. 2 is an exploded cross-sectional view of the device of FIG. 1.

Referring to FIGS. 1–7, support 12 in this embodiment has a base 16 with a generally circular configuration. In further embodiments, base 16 can have a non-circular configuration depending on the intended use of the device. Base 16 includes a top face 18 and a bottom face 20 and a central passage 22. As shown in FIG. 2, central passage 22 extends completely through support 12 to form a cavity within support 12.

A collar 24 extends from top face 18 and defines central passage 22. Collar 24 includes a top end 26, defining an inlet opening 28 to central passage 22. A flange 30 extends radially outward from top end 26 of collar 24 to form a threaded coupling member. In the embodiment of FIG. 1, the flange 30 and collar 24 form a female Luer-type fitting. Alternatively, collar 24 can be dimensioned for coupling with a catheter tubing, pump, syringe or other liquid interface.

Figure 3:
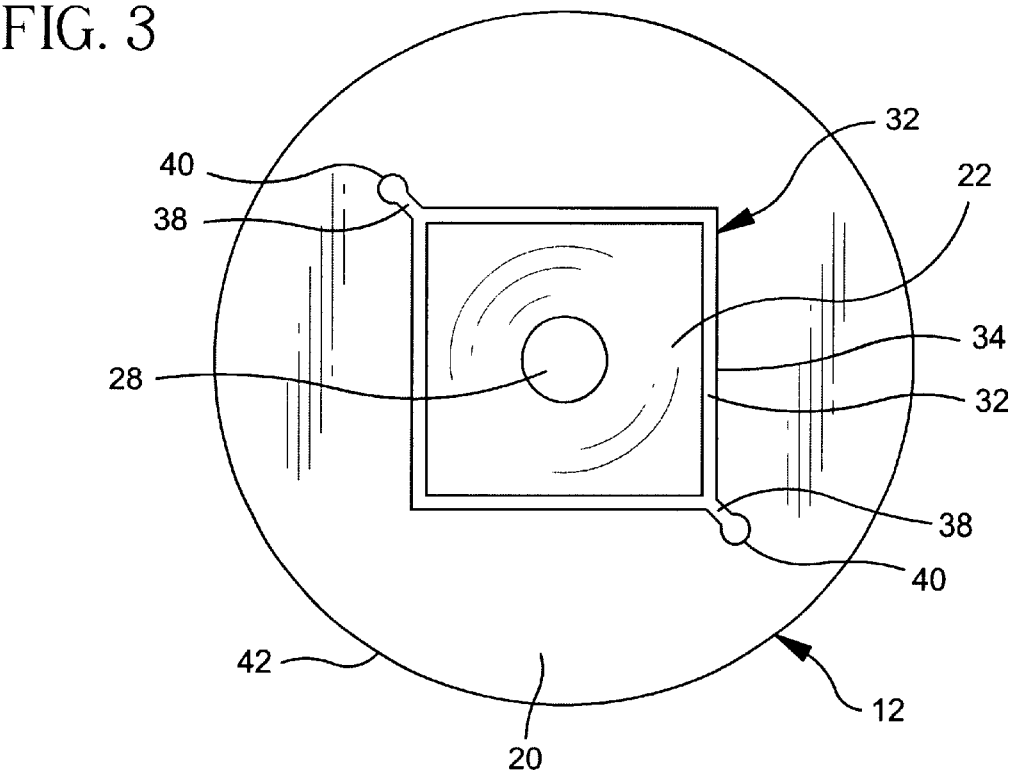
FIG. 3 is a bottom view of the device of FIG. 1 showing the support without the skin penetrating members.

Bottom face 20 of support 12 is substantially flat, as shown in FIG. 2. A recessed area 32 is formed in bottom face 20 and is in communication with central passage 22. Referring to FIGS. 2 and 3, recessed area 32 is shown as having a generally square configuration and includes a side face 34 and a bottom face 36. Side face 34 in the embodiment illustrated is substantially perpendicular to bottom face 20 of support 12. Bottom face 36 of recessed area 32 is generally perpendicular to side face 34. Generally, bottom face 36 of recessed area is parallel with bottom face 20. In alternative embodiments, recessed area 32 and microdevice 14 can have other shapes such as, for example, round or oblong. Side face 34 can be inclined inwardly or outwardly with respect to bottom face 20 of support 12.

Referring to FIG. 3, an open channel 38 formed in bottom face 20 extends outward from recessed area 32 toward an outer edge 42 of support 12. In the embodiment illustrated, two channels 38 extend from opposite corners of recessed area 32 to circular recesses 40. In an alternative embodiment, channels 38 can extend completely to outer edge 42 of bottom face 20 or omitted entirely.

Figure 4:
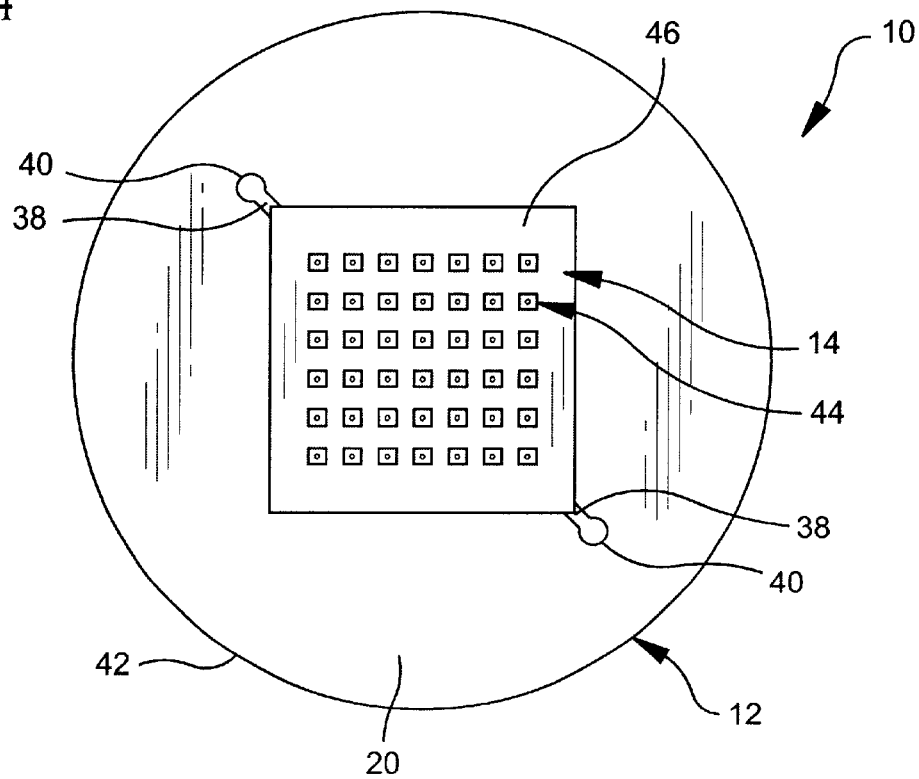
FIG. 4 is a bottom view of the device of FIG. 1 showing the skin penetrating member bonded to the support.

Microdevice 14 in the illustrated embodiments of the invention is a penetrating device suitable for use in monitoring, sampling or delivering a substance though the skin of a patient. In preferred embodiments, microdevice 14 includes a plurality of skin penetrating members 44 extending outwardly from a base 46. As used herein, the term skin penetrating member refers to a member that is able to pierce or penetrate the skin to a desired depth. Skin penetrating members 44 are shown as microneedles having a substantially square cross-sectional shape and a beveled tip 48. An axial passage 50 extends through each skin penetrating member 44 and base 46 so that axial passage 50 extends from the top face 52 to beveled tip 48. As shown in FIG. 4, skin penetrating members 44 are arranged in an array of substantially uniformly spaced apart rows and columns. The spacing between the rows and columns can be varied depending on the substance being delivered or withdrawn and the area of the skin contacted with the device. When the skin penetrating devices are microneedles, the microneedles are spaced apart about 0.05 mm to about 5 mm.

Figure 5:
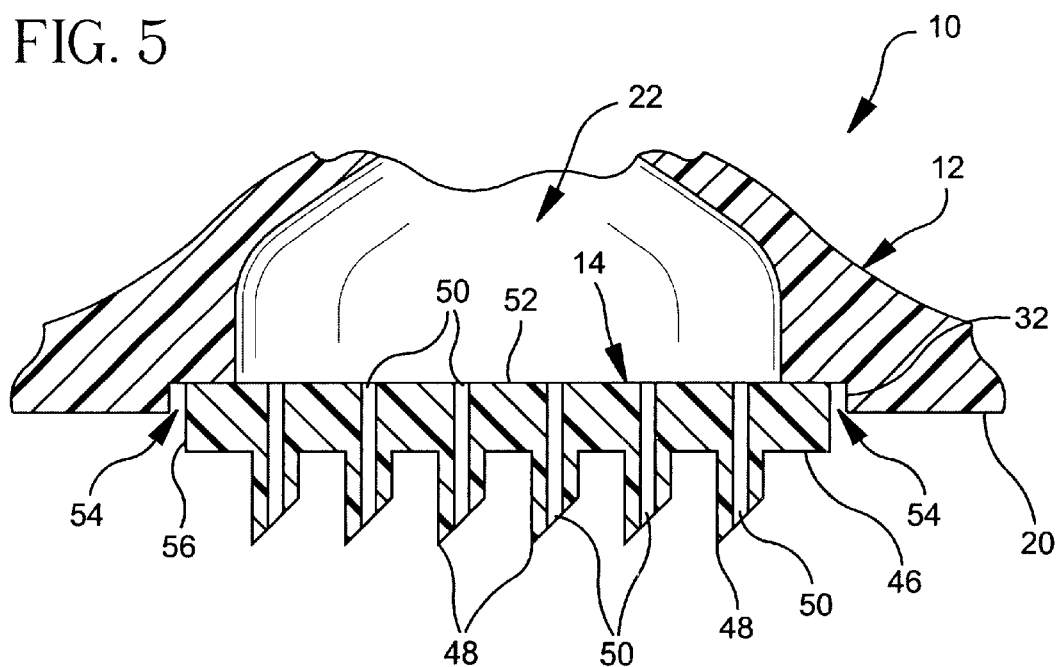
FIG. 5 is partial side elevational view in cross-section of the support and the skin penetrating member fitted in the recess of the support before bonding.
Figure 6:
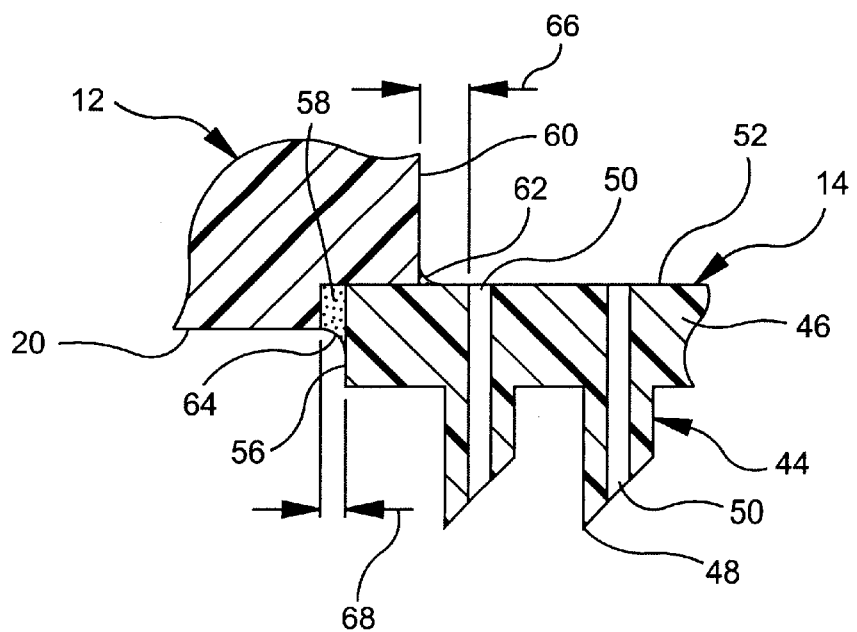
FIG. 6 is a partial side elevational view in cross-section of the device showing the bonding agent for attaching the skin penetrating device to the support.

Base 46 of microdevice 14 is dimensioned to fit within recessed area 32 as shown in FIGS. 4 and 5. In a preferred embodiment of the invention, side face 34 of recessed area 32 has a height to define a depth of recessed area 32 that is less than a thickness of base 46 of microdevice 14. As shown in FIGS. 5 and 6, recessed area 32 has a depth approximately one-half the thickness of base 46. In an alternative embodiment, recessed area 32 can have a depth substantially equal to the thickness of base 46. In one embodiment of the invention, base 46 has a thickness of about 250 microns.

In one embodiment of the invention, base 46 of microdevice 14 has a length and width slightly less than the length and width of recessed area 32 to define a gap 54 between a side edge 56 of base 46 and side face 34 of recessed area 32 as shown in FIG. 5. In further embodiments, base 46 has an outer dimension substantially equal to the dimension of recessed area 32. Device 10 is assembled by positioning microdevice 14 in recessed area 32 with a substantially uniform gap 54 formed around the perimeter of base 46. Top face 52 of base 46 preferably rests against bottom face 36 of recessed area 32 as shown in FIG. 5. In the embodiment of FIGS. 1–6, an adhesive is applied to recess 40 at the end of channel 38. The adhesive preferably has a sufficiently low viscosity to flow along channel 38 and wick into gap 54 by the surface tension of the adhesive. The adhesive fills gap 54 and surrounds base 46 to attach base 46 to support 12 and form a substantially fluid tight seal.

It has been found that the adhesive wicks between bottom face 36 of recessed area 32 and top face 52 of base 46 as shown in FIG. 6 without the need to apply a force to the adhesive. The adhesive 58 flows along top face 52 of base 46 into central passage 22 of support 12. The surface tension of adhesive 58 fills an area between a vertical side wall 60 in central passage 22 and top face 52 of base 46. The adhesive flows along the surfaces of wall 60 and top surface 52 until adhesive 58 attains a radius of curvature 62 within central passage 22 substantially equal to a radius of curvature 64 of adhesive in gap 54. Therefore, to prevent adhesive 58 from flowing into axial passage 50 of skin penetrating members 44, the space 66 between side wall 60 in central passage 22 and the innermost edge of axial passage 50 is greater than the width 68 of gap 54. Adhesive 58 can be any suitable adhesive as know in the art capable of bonding the materials together. In a preferred embodiment of the invention, the adhesive is a UV curable accelerated adhesive such as the adhesive sold under the trade name Lock-Tite 3311.

Figure 7:
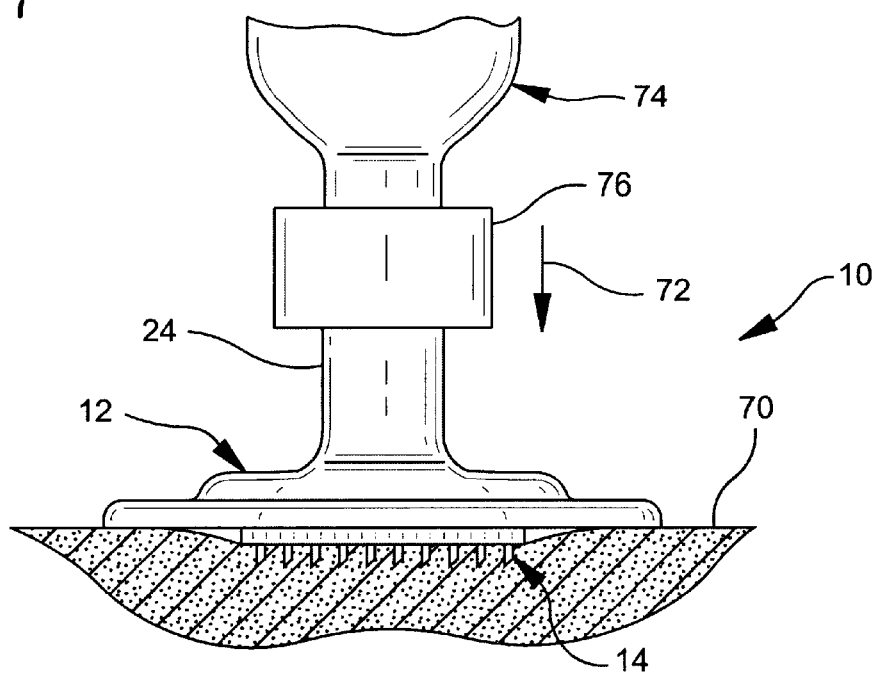
FIG. 7 is a side view showing the device in contact with the skin of a patient.

In use, device 10 is placed against the skin 70 of a patient as shown in FIG. 7 and pressed downwardly toward the skin 70 in the direction of arrow 72 to cause skin penetrating members 44 to pierce the surface of skin 70. Bottom face 20 of support 12 has a dimension to form a sealing flange against the surface of skin 70 completely surrounding microdevice 14. In the embodiment illustrated, a syringe 74 having a Luer collar 76 and is coupled to flange 30 of collar 24 to form a fluid tight seal. Syringe 74 can then be actuated to dispense a substance into or through inlet 28 to central passage 22 and through axial passages 50 of skin penetrating members 44. Syringe 74 can be actuated to apply sufficient force to deliver the substance through the skin of the patient. Alternatively, syringe 74 can be used to extract or withdraw a substance from the patient through the skin.

Bottom face 20 of support 12 can include a friction-enhancing member such as a rib or a tacky material applied to bottom face 20. Preferably, support 12 is formed from a resilient material such that support 12 is able to conform to the shape of skin 70. Bottom face 20 of support 12 forms a sealing flange to contain fluid dispensed through skin penetrating member 44 to prevent leakage and to direct the fluid into the skin or to withdraw a substance through the skin of the patient. In addition, bottom face 20 frictionally grips the skin, thereby decreasing relative motion between the support 12, skin penetrating members 44 and the skin 70. This decreases lateral sheer forces on the skin penetrating members 44 to reduce the instance of breakage and abrasion of the skin.

Support 12 is preferably made from a plastic material that is non-reactive with the substance being delivered or withdrawn from the patient. Suitable plastic materials include, for example, polyethylene, polypropylene, polyesters, polyamines, polycarbonates, and copolymers thereof as known in the art.

Microdevice 14 can also be made from suitable materials as known in the art. In one embodiment of the invention, microdevice 14 includes a plurality of microneedles formed into an array formed from spaced-apart rows and columns. The microneedles can be formed from a silicon wafer that is machined or etched to form the microneedle array. The microneedle array can also be formed from stainless steel, tungsten steel, and alloys of nickel, molybdenum, chromium, cobalt and titanium. In further embodiments, the microneedles can be formed from ceramic materials, glass polymers and other non-reactive metals. In further embodiments, microdevice 14 can be formed from needles that are mounted in a suitable base.

The skin penetrating members have a length suitable to achieve the desired depth of penetration in the skin. The length and thickness of the skin penetrating members are selected based on the substance being administered or withdrawn and the thickness of the skin in the location where the device is to be applied. In embodiments of the invention, the skin penetrating members can be microneedles, microtubes, solid or hollow needles, lancets and the like. Generally, the skin penetrating members have a length of about 100 microns to about 2,000 microns and preferably, about 250 microns to 1,000 microns. The one embodiment, the skin penetrating members are about 30-gauge to about 50-gauge needles, having a length of about 500 microns to about 1,000 microns. In the embodiment illustrated, the skin penetrating members have a substantially square cross-sectional shape. Alternatively, the skin penetrating members can be triangular, cylindrical, pyramid-shaped or flat blades.

Microdevice 14 can have a width and length as necessary to achieve the desired result. In one embodiment, microdevice 14 is about one cm$^2$ to about 10 cm$^2$. In further embodiments, microdevice 14 can have a width and length of about one centimeter to about five centimeters.

Generally, when the device is used as a delivery device, a pharmaceutical agent or drug solution is introduced into the central passage by a syringe or other fluid dispensing device. In alternative embodiments, a dried or lyophilized drug or pharmaceutical agent can be provided on the outer surfaces of the skin penetrating members or in the axial passages of the skin penetrating member. A diluent such as distilled water or saline solution can then be injected through the central passage and through the axial passage of the skin penetrating members to dissolve and reconstitute the drug or pharmaceutical agent and then deliver the drug to the patient.

Embodiment of FIGS. 8–12

A second embodiment of the invention is illustrated in FIGS. 8–12. In this embodiment, device 80 includes a support 82 and a microdevice 84 having a plurality of skin penetrating members 86.

Figure 8:
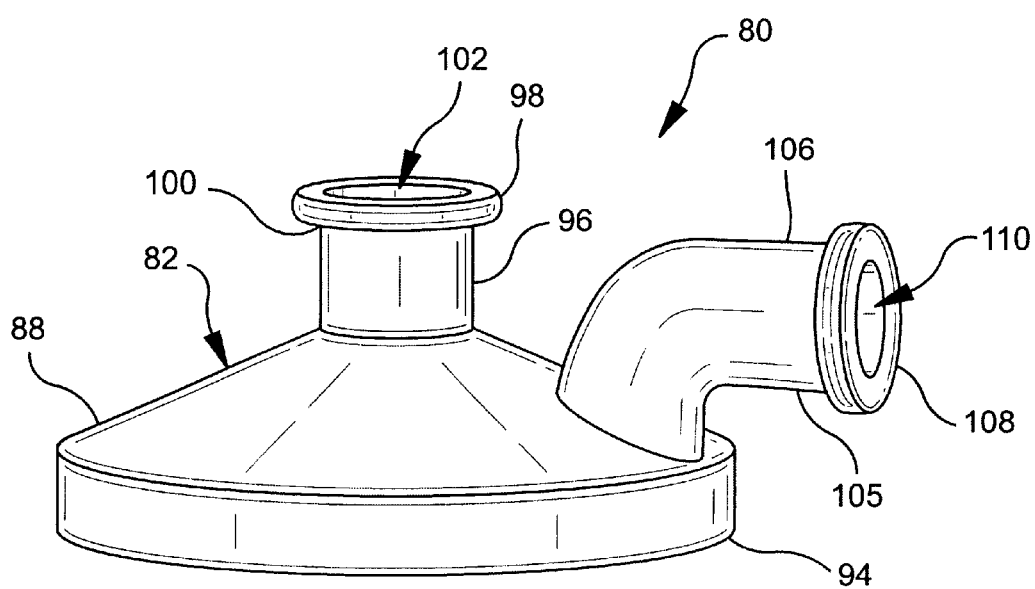
FIG. 8 is a side view of the device in a second embodiment.
Figure 9:
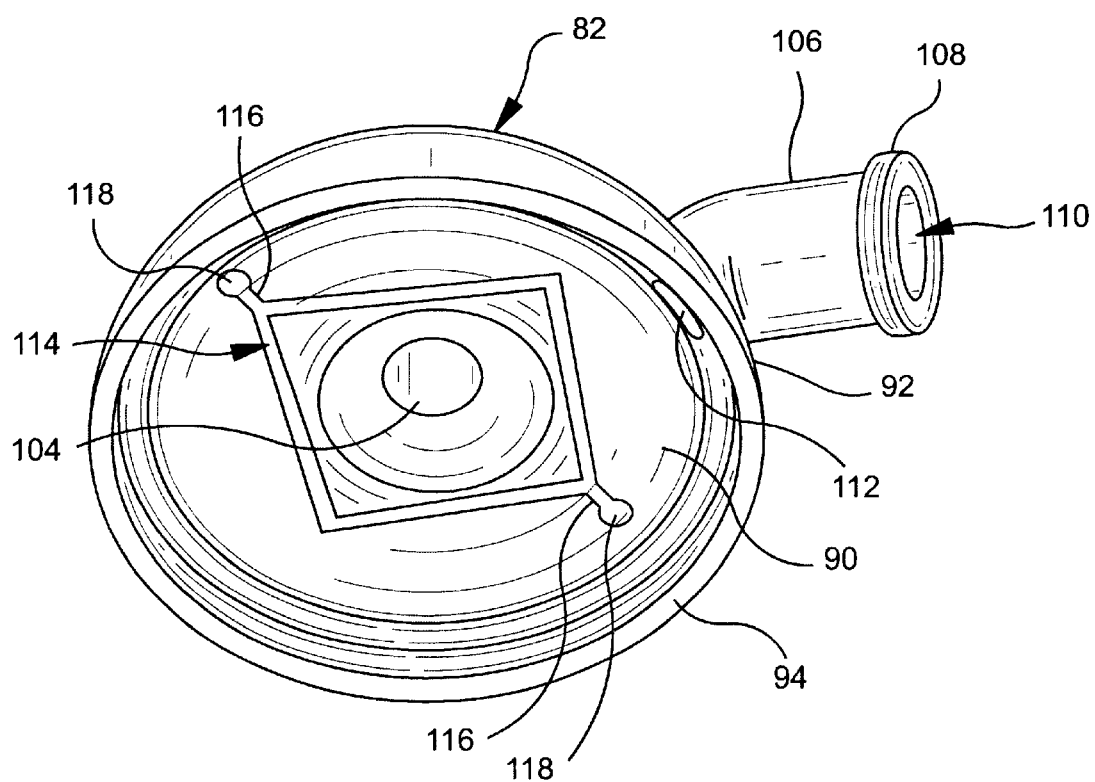
FIG. 9 is a perspective view of the device of the embodiment of FIG. 8 showing the bottom side and the recess for receiving the skin-penetrating device.
Figure 10:
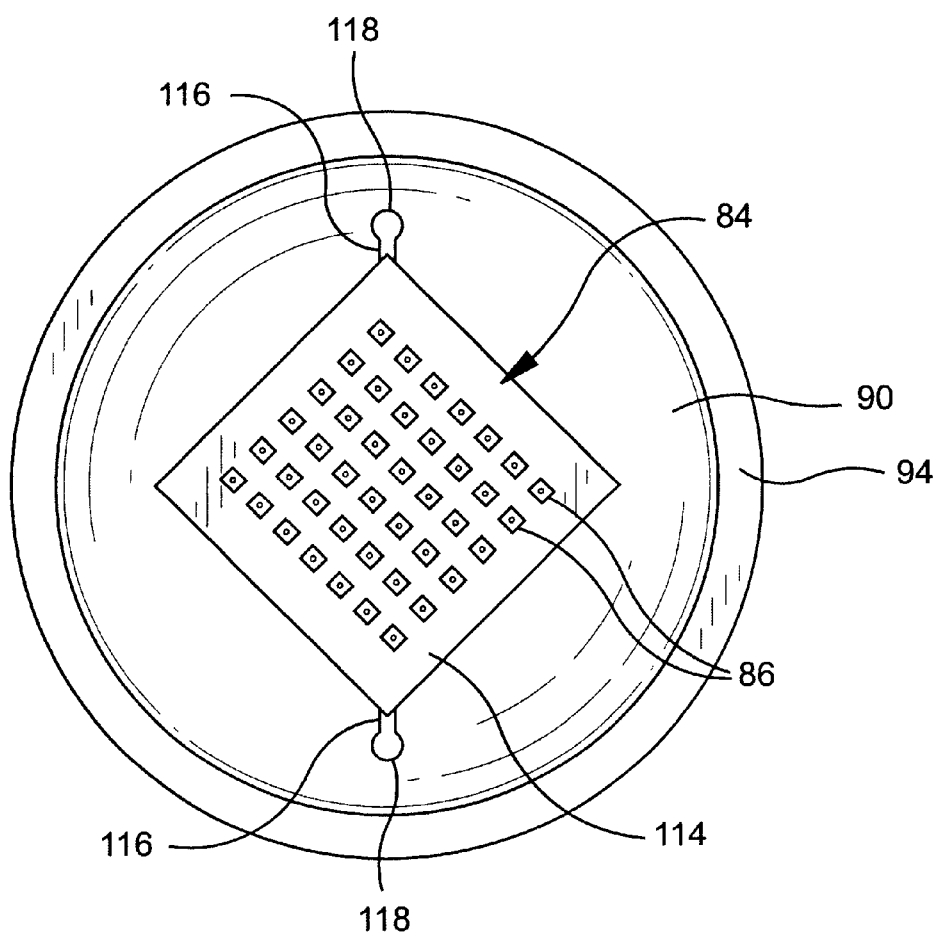
FIG. 10 is a bottom view of the device of FIG. 8 showing the skin penetrating members.

Support 82, as shown in FIGS. 8 and 9, has a substantially frustoconical top surface 88 and a bottom surface 90. Support 82 has a peripheral outer edge 92 and an annular flange 94 extending substantially perpendicular from bottom surface 90. A collar 96 extends from top surface 88 of support 82 in a generally axial direction. Collar 96 includes a flange 98 extending outwardly from a top end 100 of collar 96. An axial passage 102 extends through collar 96 to bottom surface 90 of support 82 to form a central opening 104 in bottom face 90.

A collar 106 extends from top surface 88 of support 82 and is spaced from collar 96. Collar 106 includes a flange 108 extending radially outwardly at an outer end 105. An axial passage 110 extends through collar 106 to bottom surface 90 of support 82 to form an outlet port 112 in bottom surface 90.

Figure 11:
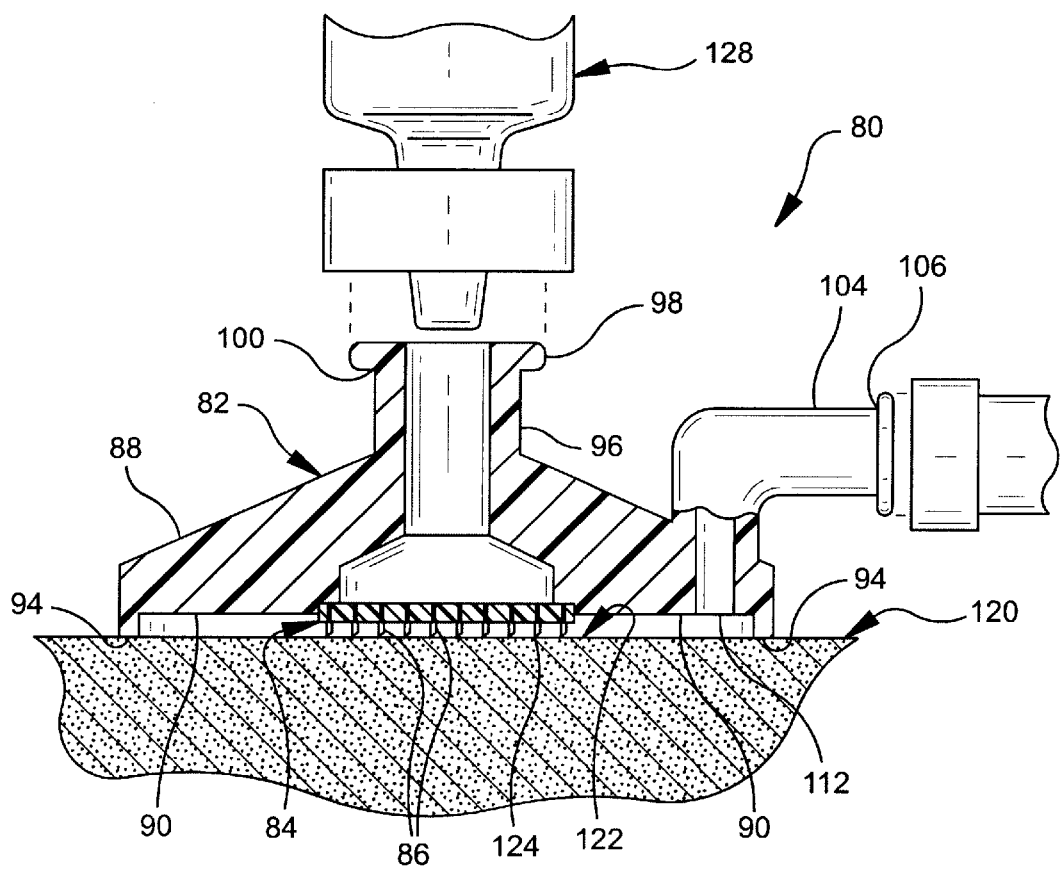
FIG. 11 is a cross sectional side view of the device of FIG. 8 in contact with the skin of a patient.
Figure 12:
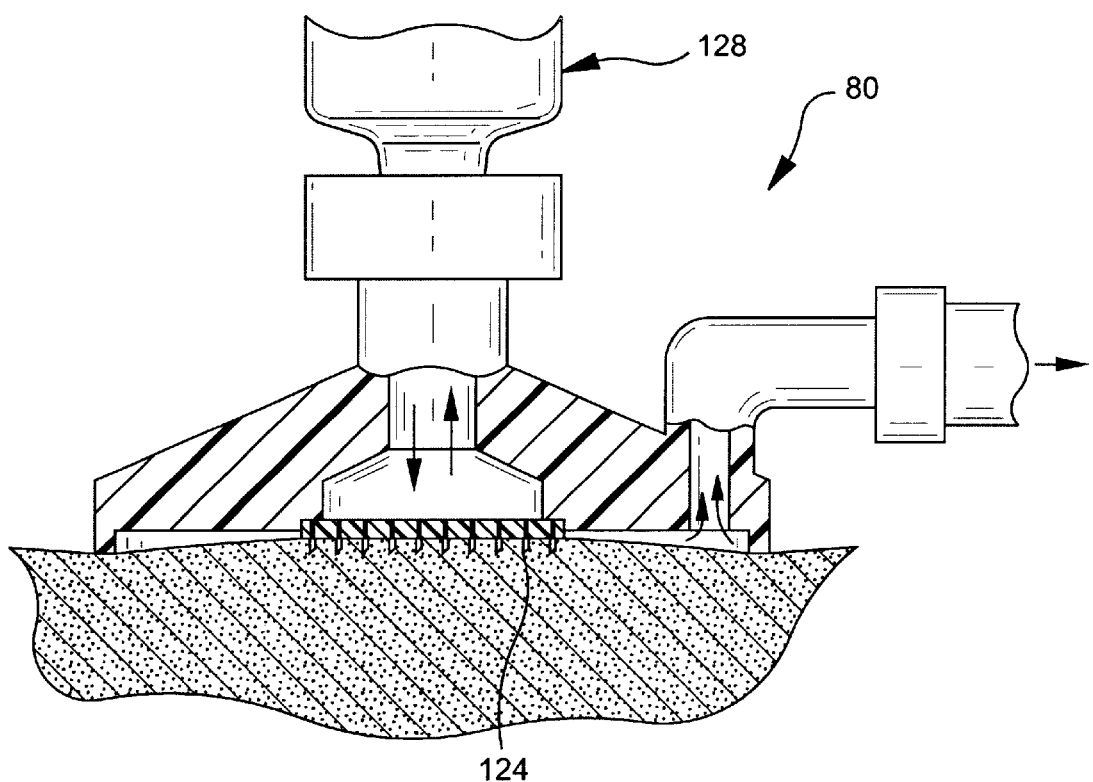
FIG. 12 is a cross sectional side view of FIG. 8 showing the penetration of skin when a vacuum is applied to the inner area of the device.

As in the previous embodiment, bottom surface 90 includes a recessed area 114 forming a ledge for receiving microdevice 84. Channels 116 and a recess forming an adhesive reservoir 118 are connected to recessed area 114 for directing an adhesive to recessed area 114 to bond microdevice 84 to support 82. In further embodiments, channels 116 and reservoir 118 can be omitted and the microdevice bonded to the support by ultrasonic welding, thermal welding or insert molding by molding the support directly onto the microdevice. In use, device 80 is placed against the skin 120 as shown in FIG. 11. Device 110 is positioned with flange 94 contacting skin 120 and encircling a target area 122. In one embodiment, flange 94 has an axial length to lie in a plane that is parallel with the tips 124 of skin penetrating members 86.

Device 80 is pressed against the skin 120 and a suitable vacuum source is coupled to collar 106. In one embodiment, the vacuum source is a syringe having a Luer lock collar threaded onto flange 108 of collar 106. The plunger of the syringe can be extracted to create a reduced pressure in the target area 122 which pulls the skin upwardly into contact with skin penetrating members 86. Pulling the skin upwardly by reducing the pressure in the space between bottom wall 90 and skin 120 enables skin penetrating members 86 to penetrate or pierce the skin substantially uniformly across the width of microdevice 84. Generally, the vacuum source is maintained during the sampling or delivery of a substance to maintain penetration of the skin by the skin penetrating members. In addition, maintaining the vacuum prevents movement of the device with respect to the skin to prevent breakage of the skin penetrating members and abrasion of the skin. In alternative embodiments, a vacuum pump or other suitable device capable of drawing a vacuum or reduced pressure can be coupled to collar 106.

After the skin penetrating members have adequately penetrate or pierced the skin to a desired depth, a supply or sampling container, such as a syringe 128, is coupled to collar 96 using a Luer type fitting. When a substance is to be sampled or withdrawn from the patient, the syringe plunger is withdrawn to reduce the pressure in the central area of support 82 to withdraw a fluid through the axial passage in the skin penetrating members. Alternatively, a substance can be delivered to the patient by directing the substance to the central passage of support 82 and through the axial passage of skin penetrating member 86. A substance can be delivered to a patient under pressure as an active delivery system or without pressure as a passive delivery system. The device is left in contact with the skin for sufficient time to withdraw the desired substance or deliver the substance to the patient. The time required is dependent on the substance being delivered or withdrawn, the volume of the substance, and the target area on the skin.

The device of the invention is generally designed to be a disposable, single-use device. The device can be used safely and effectively for intradermal delivery of a pharmaceutical agent or other substance. The device is particularly suitable for introducing a vaccine intradermally for efficiently delivering a small amount of a vaccine antigen for presentation to the Langerhans cells. The length, width and spacing of the microneedles can vary depending on the pharmaceutical agent being administered or required to penetrate the stratum corneum to the optimum depth for the specific pharmaceutical agent being administered. When delivering a vaccine, the microneedles are dimensioned to target the optimum intradermal delivery site to promote the desired immune response.

While various embodiments have been chosen to illustrate the invention, it will be appreciated by those skilled in the art that various additions and modifications can be made to the invention without departing from the scope of the invention as defined in the appended claims.

What is claimed is:

1. A method of forming a microdevice for delivering or withdrawing a substance through the skin of a patient, comprising the steps of:

providing a support having a bottom face with a recessed area having a dimension less than a dimension of said bottom face, positioning a skin penetrating device in said recessed area of said support, said skin penetrating device having a base and at least one skin penetrating member, said base having a dimension less than said dimension of said recessed area, and applying a bonding amount of a bonding agent to at least one location between said support and said base in said recessed area, said bonding agent having a viscosity to wick between said base and said support.

2. The method of claim 1, wherein said base is a silicon wafer and said skin penetrating member is a microneedle array.

3. The method of claim 1, wherein said base has a thickness of about 250 microns.

4. The method of claim 1, wherein said recessed area has a depth equal to or less than a thickness of said base.

5. The method of claim 1, wherein said recessed area has a bottom surface parallel with said bottom face of said support and a side face extending between said bottom face of said support and said bottom surface of said recess, said method comprising positioning said skin penetrating device on said bottom surface.

6. The method of claim 5, wherein said side face of said recessed area is substantially perpendicular to said bottom face of said support.

7. The method of claim 5, wherein said recessed area is dimensioned to define a gap between said side face and said base of said skin penetrating member, and said method comprises applying said bonding agent to said gap.

8. The method of claim 1, wherein said support includes at least one channel communicating with said recessed area, said method comprising applying said bonding agent to said channel whereby said bonding agent flows into said recessed area.

9. The method of claim 8, wherein said at least one channel is an open channel on said bottom face of said support.

10. The method of claim 8, wherein said at least one channel has a first end connected to said recessed area and a second end connected to a reservoir formed in said support, said method comprising applying said bonding agent to said reservoir whereby said bonding agent flows through said at least one channel to said recessed area.

11. The method of claim 1, wherein said support has a cavity communicating with said recessed area.

12. The method of claim 11, wherein said support includes an opening extending from a top face to said cavity.

13. The method of claim 10, wherein said support has at least one port communicating with said bottom face, said at least one port being spaced from said recessed area.

14. The method of claim 1, wherein said base of said penetrating device is a silicon wafer and said at least one skin penetrating member is an array of microneedles.

15. The method of claim 1, wherein said skin penetrating device includes at least one passage extending through said base and being in communication with said at least one skin penetrating member.

16. A method of withdrawing a substance or delivering a substance through the skin of a patient, said method comprising providing a support having a central passage, a bottom face, a one skin penetrating device on said bottom face, said central passage being in communication with said skin penetrating device, positioning said support on the skin of a patient with said bottom face of said support and said at least one skin penetrating device contacting said skin, reducing the pressure in an area between said support and said skin to draw said skin toward said skin penetrating member and to cause said skin penetrating device to penetrate said skin, and withdrawing or delivering a substance through the skin of said patient.

17. The method of claim 16, wherein said bottom face of said support includes a recessed area having a dimension less than a dimension of said bottom face, and wherein said skin penetrating device includes a base fitted in said recessed area and coupled to said support.

18. The method of claim 16, wherein said support has an outer edge spaced from and surrounding said at least one skin penetrating member and an annular flange coupled to said outer edge and extending away from said support.

19. The method of claim 18, wherein said support further includes an outlet port communicating with said bottom face of said support between said annular flange and said skin penetrating member, and said method comprises applying a vacuum source to said outlet port to reduce the pressure between said support and said skin.

20. The method of claim 16, wherein said skin penetrating device includes an axial passage in communication with said central passage of said support.

21. The method of claim 16, wherein said at least one skin penetrating device comprises an array of skin penetrating members, said skin penetrating members being selected from the group consisting of microtubes, microneedles, cannulas, blades and lancets.

22. The method of claim 16, wherein said support includes a fluid coupling communicating with said central passage, said method comprising withdrawing or supplying a substance through said fluid coupling to said central passage.

23. The method of claim 19, comprising coupling a vacuum source to said outlet port and drawing a vacuum through said coupling.

24. A device for delivering or withdrawing a substance from a patient, said device comprising:

a support member having a bottom face and a recessed area having a dimension less than a dimension of said bottom face, a skin penetrating device having a base and at least one skin penetrating member, said base being positioned within said recessed area of said support, and a bonding material attaching said skin penetrating device to said support member and filling a space between said recessed area and said base of said skin penetrating device.

25. The device of claim 24, wherein said base is a silicon wafer and said skin penetrating member is a microneedle array.

26. The device of claim 24, wherein said base has a thickness of about 250 microns.

27. The device of claim 24, wherein said recessed area has a bottom surface parallel with said bottom face of said support and a side face extending between said bottom face of said support and said bottom surface of said recess.

28. The device of claim 27, wherein said side face of said recessed area is substantially perpendicular to said bottom face of said support.

29. The device of claim 24, wherein said support includes at least one channel communicating with said recessed area for directing said bonding material into said recessed area.

30. The device of claim 29, wherein said at least one channel is an open channel on said bottom face of said support.

31. The device of claim 24, wherein said support has at least one port communicating with said bottom face of said support between an outer edge of said support and said skin penetrating device.

32. The device of claim 24, wherein said skin penetrating device includes at least one passage extending through said base and being in communication with said at least one skin penetrating member.

33. The device of claim 32, wherein said support includes a port and a central passage communicating with said skin penetrating device for delivering or withdrawing a fluid through said device.

34. The device of claim 24, wherein said support has an outer edge spaced from and surrounding said skin penetrating device and a flange extending from said outer edge away from said bottom face of said support.

35. The device of claim 34, wherein said flange is dimensioned to contact the skin of a patient and wherein said flange includes a friction enhancing member.

36. The device of claim 35, wherein said friction enhancing member is a ridge.

37. The device of claim 35, wherein said friction enhancing member is a tacky material.

38. The device of claim 34, wherein said support further comprises a port communicating with said bottom face of said support between said flange and said skin penetrating device, and an outlet coupling communicating with said port.

39. A device for delivering or withdrawing a substance from a patient, said device comprising:

a support member having a bottom face, an outer edge, and a recessed area having a dimension less than a dimension of said bottom face, said support having at least one passage communicating with said bottom face between said recessed area and said outer edge, a skin penetrating device having a base and at least one skin penetrating member, said base being positioned within said recessed area and coupled to said support.

40. The device of claim 39, wherein said support includes a port and a central passage communicating with said skin penetrating device for delivering or withdrawing a fluid through said device.

41. The device of claim 40, further comprising a flange on said outer edge extending away from said bottom face.

42. The device of claim 41, wherein said flange is dimensioned to contact the skin of a patient and includes a friction enhancing member.

43. The device of claim 41, wherein said skin penetrating member is a microneedle array.

44. A method of forming a microdevice, comprising the steps of:

providing a support having a bottom face with a recessed area having a dimension less than a dimension of said bottom face and at least one channel with said recessed area, positioning a microdevice in said recessed area of said support, said microdevice having a base with a dimension less than said dimension of said recessed area, and applying a bonding amount of a bonding agent to said channel, said bonding agent having a viscosity to wick along said channel and between said base and said support.

45. The method of claim 44, wherein said at least one channel is an open channel on said bottom face of said support.

46. The method of claim 45, wherein said at least one channel has a first end connected to said recessed area and a second end connected to a reservoir formed in said support, said method comprising applying said bonding agent to said reservoir whereby said bonding agent flows through said at least one channel to said recessed area.

* * * * *